(12) United States Patent
Duggan

(10) Patent No.: US 7,951,777 B2
(45) Date of Patent: May 31, 2011

(54) COMPOSITIONS AND METHODS FOR TREATMENT OF CARDIOVASCULAR DISEASE

(75) Inventor: Karen A. Duggan, New South Wales (AU)

(73) Assignee: Vectus Biosystems Limited, New South Wales (AU)

( * ) Notice: Subject to any disclaimer, the term of this patent is extended or adjusted under 35 U.S.C. 154(b) by 817 days.

(21) Appl. No.: 11/629,041

(22) PCT Filed: Jun. 10, 2005

(86) PCT No.: PCT/AU2005/000835
§ 371 (c)(1),
(2), (4) Date: Dec. 8, 2006

(87) PCT Pub. No.: WO2005/120545
PCT Pub. Date: Dec. 22, 2005

(65) Prior Publication Data
US 2008/0108573 A1  May 8, 2008

(30) Foreign Application Priority Data
Jun. 11, 2004 (AU) .............................. 2004903188

(51) Int. Cl.
*A61K 38/22* (2006.01)
*C07K 14/575* (2006.01)
(52) U.S. Cl. ..................................................... 514/13.1
(58) Field of Classification Search .................. None
See application file for complete search history.

(56) References Cited

U.S. PATENT DOCUMENTS

| | | | | |
|---|---|---|---|---|
| 3,862,927 | A | * | 1/1975 | Said et al. ........... 530/324 |
| 3,880,826 | A | | 4/1975 | Said et al. |
| 4,835,252 | A | * | 5/1989 | Musso et al. ........ 530/324 |
| 4,939,224 | A | | 7/1990 | Musso et al. |
| 6,217,886 | B1 | * | 4/2001 | Onyuksel et al. ..... 424/401 |
| 2005/0075290 | A1 | | 4/2005 | Gandhi |

FOREIGN PATENT DOCUMENTS

| | | | |
|---|---|---|---|
| WO | WO-88/03928 | | 6/1988 |
| WO | WO-01/34088 | | 5/2001 |
| WO | WO-02/43746 A2 | | 6/2002 |
| WO | WO2005120545 | * | 12/2005 |
| WO | WO2007065226 | * | 6/2007 |

OTHER PUBLICATIONS

Markos et al. An Evaluation of the Efficacy of Vasoactive Intestinal Polypeptide Antagonists in vivo in the Anaesthetized Dog. Pharmacology, 2002. vol. 66, pp. 206-210.*
Davis et al., "The Effects of a High Sodium Diet on the Metabolism and Secretion of Vasoactive Intestinal Peptide in the Rabbit," Journal of Physiology (1992), 451, pp. 17-23.
Delgado et al., "Vasoactive intestinal peptide prevents experimental arthritis by downregulating both autoimmune and inflammatory components of the disease," Nature Medicine, (2001), vol. 7, No. 5, pp. 563-568.
Duggan et al., "Angiotensin-Converting Enzyme Inhibition with Enalapril Increases the Cardiac Concentration of Vasoactive Intestinal Peptide," Annals of the New York Academy of Sciences (1996), vol. 805, pp. 713-716.
Hughes et al., "Arterial myogenic properties of the spontaneously hypertensive rat," Experimental Physiology (2002), vol. 87.5, pp. 527-534.
Humphrey et al., "Hepatic and Pulmonary Clearance of Exogenous Vasoactive Intestinal Peptide in the Rat," Gastroenterology (1979), vol. 77(1), pp. 55-60.
International Search Report, International Application No. PCT/AU2005/000835.
Kalfin et al., "Protective Role of Intracoronary Vasoactive Intestinal Peptide in Ischemic and Reperfused Myocardium," The Journal of Pharmacology and Experimental Therapeutics (1994), vol. 268, No. 2, pp. 952-268.
Pechanova et al., "Positive therapeutic effects of red wine polyphenols in pexperimental hypertension," Bulletin OIV, 859-860, 678-697 (English translation) (an English translation is provided.).
Sacerdote et al., "Vasoactive Intestinal Peptide 1-12: A Ligand for the CD4 (T4)/Human Immunodeficiency Virus Receptor," Journal of Neuroscience Research (1987), vol. 18, pp. 102-107.
Saetrum Opgaard et al., "Vasoactive intestinal peptide has a direct positive inotropic effect on isolated human myocardial trabeculae," Clinical Science (2001), vol. 101 pp. 637-643.
Sole, et al., "A Possible Change in the Rate-Limiting Step for Cardiac Norepinephrine Synthesis in the Cardiomyopathic Syrian Hamster," Circulation Research (Dec. 1977), vol. 41, No. 6, pp. 814-817.
Tsybouleva et al. "Aldosterone, through novel signaling proteins, is a fundamental molecular bridge between the genetic defect and the cardiac phenotype of hypertrophic cardiomyopathy," Circulation Mar 16, 2004, 109(10), pp. 1284-1291 (Abstract).
Tsybouleva et al. "Aldosterone, through novel signaling proteins, is a fundamental molecular bridge between the genetic defect and the cardiac phenotype of hypertrophic cardiomyopathy," Circulation Mar 16, 2004, 109(10), pp. 1284-1291.
Unverferth et al., "Effect of vasoactive intestinal polypeptide on the canine cardiovascular system," J. Laboratory & Clinical Medicine (1985), vol. 106, No. 5, pp. 542-550.
Unverferth et al., "The evolution of β-adrenergic dysfunction during the induction of canine cobalt cardiomyopathy," Cardiovascular Research (1984), 18, pp. 44-50.
Ye et al., "Early myocardial fibrosis is associated with depletion of vasoactive intestinal peptide in rat heart," Experimental Physiology (2002), vol. 87.5, pp. 539-546.
Ye et al., "Vasopeptidase inhibition reverses myocardial vasoactive intestinal peptide depletion and decreases fibrosis in salt sensitive hypertension." European Journal of Pharmacology, (2004), vol. 485, pp. 235-242.
Ye et al., "Myocardial vasoactive intestinal peptide and fibrosis induced by nitric oxide snythase inhibition in the rat," Scandinavian Physiological Society, (2003), vol. 179, pp. 353-360.

* cited by examiner

*Primary Examiner* — Marcela M Cordero Garcia
(74) *Attorney, Agent, or Firm* — Goodwin Procter LLP

(57) ABSTRACT

The present invention is concerned with composition and methods for treatment of certain cardiovascular conditions. In particular it is concerned with prophylactic or therapeutic treatment of myocardial fibrosis or associated conditions by administering compositions comprising vasoactive intestinal peptide (VIP) and/or active fragments) thereof.

9 Claims, 10 Drawing Sheets

SEQUENCE LISTING

<160> NUMBER OF SEQ ID NOS: 3

<210> SEQ ID NO 1
<211> LENGTH: 28
<212> TYPE: PRT
<213> ORGANISM: Homo sapiens

<400> SEQUENCE: 1

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 2

```
-continued

<211> LENGTH: 12
<212> TYPE: PRT
<213> ORGANISM: Homo sapiens

<400> SEQUENCE: 2

His Ser Asp Ala Val Phe Thr Asp Asn Tyr Thr Arg
1               5                   10

<210> SEQ ID NO 3
<211> LENGTH: 23
<212> TYPE: PRT
<213> ORGANISM: Homo sapiens

<400> SEQUENCE: 3

Phe Thr Asp Asn Tyr Thr Arg Leu Arg Lys Gln Met Ala Val Lys Lys
1               5                   10                  15

Tyr Leu Asn Ser Ile Leu Asn
            20
```

COMPOSITIONS AND METHODS FOR TREATMENT OF CARDIOVASCULAR DISEASE

This application is the U.S. national stage application of International (PCT) Patent Application No. PCT/AU2005/000835, filed Jun. 10, 2005, which claims the benefit of AU Application No. 2004903188, filed Jun. 11, 2004. The entire disclosures of these two applications are hereby incorporated by reference as if set forth at length herein in their entirety.

TECHNICAL FIELD

This invention relates to compositions and methods for therapeutic or prophylactic treatment of myocardial fibrosis or associated conditions.

BACKGROUND

Any discussion of the prior art throughout the specification should in no way be considered as an admission that such prior art is widely known or forms part of common general knowledge in the field.

In myocardial fibrosis, heart muscle is replaced by fibrous or scar tissue. This can interfere with the flexibility of the heart muscle. It can lead to a decrease in function and, eventually, to overt heart failure In Australia, congestive cardiac failure affects one percent of the general population and three to five percent of those aged over 65, rising to ten to twenty percent of the population aged 80 or over.

Congestive cardiac failure is the most common cause of hospital admission in adult medicine. The annual mortality in admitted patients varies from 10 to 20% in those with mild to moderate symptoms to 40 to 60% in those with severe heart failure. The impact of these admissions and the cost to the community is such that at least two State Governments in Australia have funded programs to improve the management of heart failure. However, these are late stage programs which, while they may curtail admissions in patients with established severe disease, do not address underlying mechanisms. Thus there is a substantial need to reduce or prevent admissions and especially to prevent and/or reverse myocardial fibrosis and its progression, ultimately to the end stage.

The pathologic basis underlying congestive cardiac failure is the development of myocardial fibrosis. This commences as perivascular fibrosis and then extends into the interstitium, becoming more generalised, and resulting in diastolic dysfunction and/or eventually, overt heart failure. There have been numerous studies on humans and animals and these have suggested various factors relevant to myocardial fibrosis, including genetic predisposition, ischaemic heart disease, hypertension, nitric oxide deficiency, oxidative stress, dietary salt intake and various other factors.

In a study of the effect of low, intermediate or high sodium diets fed to rats, the degree of myocardial fibrosis increased with increasing dietary sodium intake. It was found that there was a negative correlation between the concentration of vasoactive intestinal peptide (VIP) in the heart and the degree of myocardial fibrosis (Experimental Physiology (2002) 87.5, 539-546). This study suggested that the decrease in myocardial VIP concentration may play a pathogenic role in the development of myocardial fibrosis.

Vasoactive intestinal peptide (VIP) was first purified in or around the mid-1970's and then synthesised.

U.S. Pat. No. 4,939,224 discusses numerous and varied biological activities of VIP. These include smooth muscle relaxation, inducement of vasodilatation, stimulation of intestinal secretion of water and electrolytes, neuroregulation, stimulation of the production of pancreatic juice and inhibition of gastric acid secretion. However, there are significant deleterious side effects, including hypotension, tachycardia and flushing.

Because VIP was known to exert vasodilatory action and positive ionotropic effect on the heart, its role in myocardial ischaemia was examined (19: J Pharmacol Exp Ther 1994 February; 268(2):952-8). The study was conducted on isolated rat heart. The study found that a significant amount of VIP was released from the ischaemic reperfused heart. In a follow up experiment, the isolated rat heart was perfused with VIP, ischaemia was induced and then the coronary flow was terminated, followed by reperfusion. The study indicated a significant improvement of myocardial function by VIP, evidenced by enhanced left ventricular functions and coronary flow and the reduction of tissue injury.

A study was carried out on isolated trabeculae from the right atrium and left ventricle of human hearts (Clinical Science (2001) 101, 637-643). The hearts were taken from previously healthy individuals who had died from cerebrovascular accidents or head trauma. The study found that VIP had a direct positive ionotropic effect in both the atria and the ventricles of the human heart.

In the study referred to above (Experimental Physiology (2002) 87.5, 529-546), the experiments were conducted on hearts removed from rats treated with sodium diets. This in vitro study found that there was a significant correlation between decreasing myocardial VIP concentration and increasing degree of myocardial fibrosis in the heart. This suggested that VIP depletion in the heart may play a role in the development of fibrosis.

Despite the results of the in vitro studies, it had been found previously that injected VIP was not taken up by the normal heart (Gastroenterology (1979) 77.1, 55-60). The inability of the normal heart to take up injected VIP, indicated that VIP had no role as an effective therapeutic for treatment or prevention of myocardial fibrosis.

It is an object of the present invention to overcome or ameliorate at least one of the disadvantages of the prior art, or to provide a useful alternative.

SUMMARY OF THE INVENTION

Accordingly, in a first aspect the invention provides a composition for prophylactic or therapeutic treatment of myocardial fibrosis or an associated condition, the composition including a pharmaceutically effective amount of one or more of vasoactive intestinal peptide (VIP) (SEQ ID No. 1) and active fragments thereof, optionally in combination with a pharmaceutically acceptable carrier.

The pharmaceutically effective amount of VIP or an active fragment will vary according to the patient and/or with the severity of the disease or condition. These variables can be ascertained by one skilled in the art by routine experimentation. An appropriate dosage range, as a starting point, can be derived from dosages administered in the animal models described herein and the plasma levels achieved. Such parameters can be easily ascertained by simple routine measurements.

The preferred active fragments of VIP are VIP (1-12) (SEQ ID No. 2) and VIP (6-28) (SEQ ID No. 3).

The compositions of the invention may be administered in conjunction with a pharmaceutically acceptable carrier, which may be any of those known in the art or devised hereafter and suitable for the intended use. As well as carriers, the pharmaceutical composition of the invention may include other ingredients, including dyes, preservatives, buffers and anti-oxidants, for example. The compositions of the present invention may also include other active agents useful in the treatment of cardiovascular conditions.

The pharmaceutical composition of the invention may take any suitable form, but is preferably suitable for administration by intravenous, intramuscular or subcuticular injection while active VIP fragments may be suitable for oral administration. However, if appropriately formulated, VIP may also be administered orally. Other methods of administration such as patches, snuffs, nasal sprays and the like will be clear to those skilled in the art.

According to a second aspect the invention provides a method of therapeutic treatment of myocardial fibrosis or an associated condition in a subject, the method including administering to the subject with myocardial fibrosis or an associated condition, a composition according to the invention.

The pharmaceutical compositions of the invention may be used to prevent or slow down progression of established myocardial fibrosis, as well as to reduce the degree of established fibrosis.

According to a third aspect the invention provides a method of prophylactic treatment of myocardial fibrosis or an associated condition in a subject, the method including administering to the subject at risk of developing myocardial fibrosis or an associated condition, a composition according to the invention.

With respect to prophylactic treatment it will be understood that such a treatment would benefit particularly subjects who are at risk of developing myocardial fibrosis or an associated condition. As an example of subjects in the risk category are those having hypertension, diabetes, myocarditis, ischaemic heart disease, drugs such as daunorubicin and others which are used in cancer chemotherapy, genetic predisposition, other conditions such as Conn's Syndrome and Phaeochromocytoma, high salt diet and the like. The prophylactic treatment may be used to prevent or slow down the development of fibrosis in the at risk group. High proportion of subjects may already have signs of early heart failure on echocardiography. For example such signs are present in nearly 80% of patients with hypertension. The incidence in diabetics is even higher.

According to a fourth aspect the invention provides a method of prophylactic or therapeutic treatment of congestive cardiac failure in a subject, the method including administering to the subject at risk of developing congestive cardiac failure, a pharmaceutical composition according to the invention.

According to a fifth aspect the invention provides a method of reducing the levels, inhibiting or reducing the production, of pro-fibrotic mediators in a subject, the method including administering to the subject a composition according to the invention.

According to a sixth aspect the invention provides a method of elevating the VIP content of the cardiac muscle in a subject with myocardial fibrosis or a related condition, or a subject at risk of developing myocardial fibrosis or an associated condition, including administering to the subject a composition according to the invention.

According to a seventh aspect the invention provides a method of reducing collagen formation or enhancing collagen degradation in the cardiac muscle of a subject, the method including administering to the subject a composition according to the invention.

It will be apparent to one skilled in the art that the pattern of use of the pharmaceutical compositions of the invention may need to be altered for optimum effect. It may be necessary to take into account the nature of the disease or condition as well as its severity.

The associated conditions, which may be subject to prevention or treatment by the pharmaceutical compositions of the invention, may include left ventricular hypertrophy, diastolic dysfunction, myocarditis, cardiomyopathy, left ventricular dysfunction and congestive cardiac failure (for which myocardial fibrosis may be an underlying pathology). The associated condition may also include conditions which give rise to generation of profibrotic mediators or conditions which predispose a subject to myocardial fibrosis, such as for example hypertension and/or high salt intake, diseases such as diabetes and the like.

Further aspect of the invention includes the use of compositions of the invention in the manufacture of a medicament for the prophylactic or therapeutic treatment of myocardial fibrosis, or an associated condition.

Yet another aspect of the invention provides the use of compositions of the invention in the manufacture of a medicament for the prophylactic or therapeutic treatment of congestive cardiac failure.

DESCRIPTION OF THE PREFERRED EMBODIMENT

Figure 1:
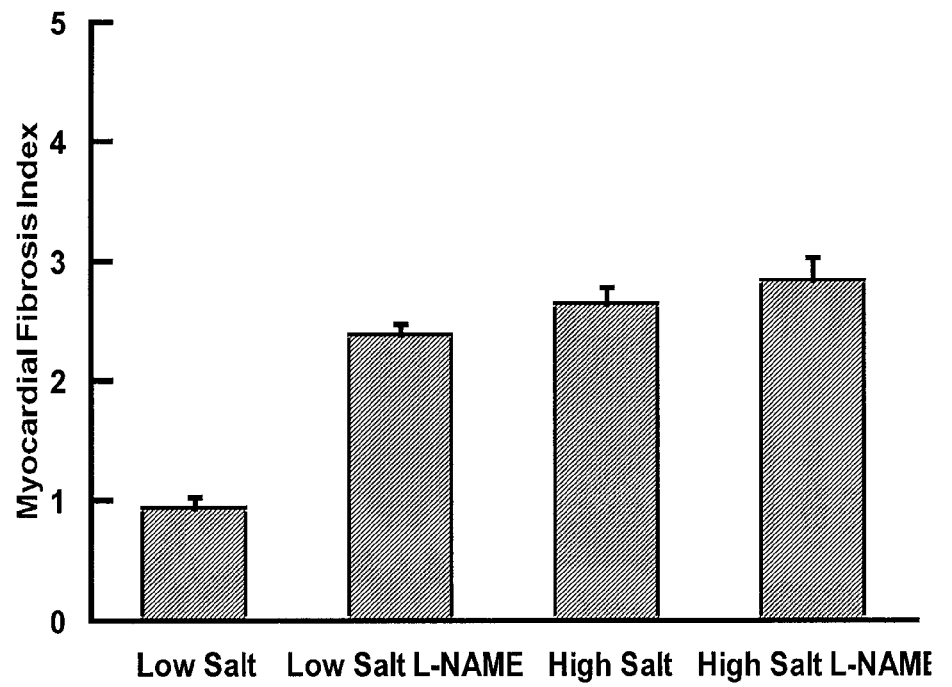
FIG. 1: Levels of myocardial fibrosis in a number of models of myocardial fibrosis (left hand panel). Right hand panel shows difference between mean myocardial VIP concentrations in the four models after a one hour infusion of VIP (SEQ ID No. 1) or vehicle. The difference between the mean myocardial VIP concentration after VIP or vehicle infusion represents a measure of VIP uptake by the myocardium. As fibrosis worsens the amount of VIP taken up by the heart increases.
Figure 1:
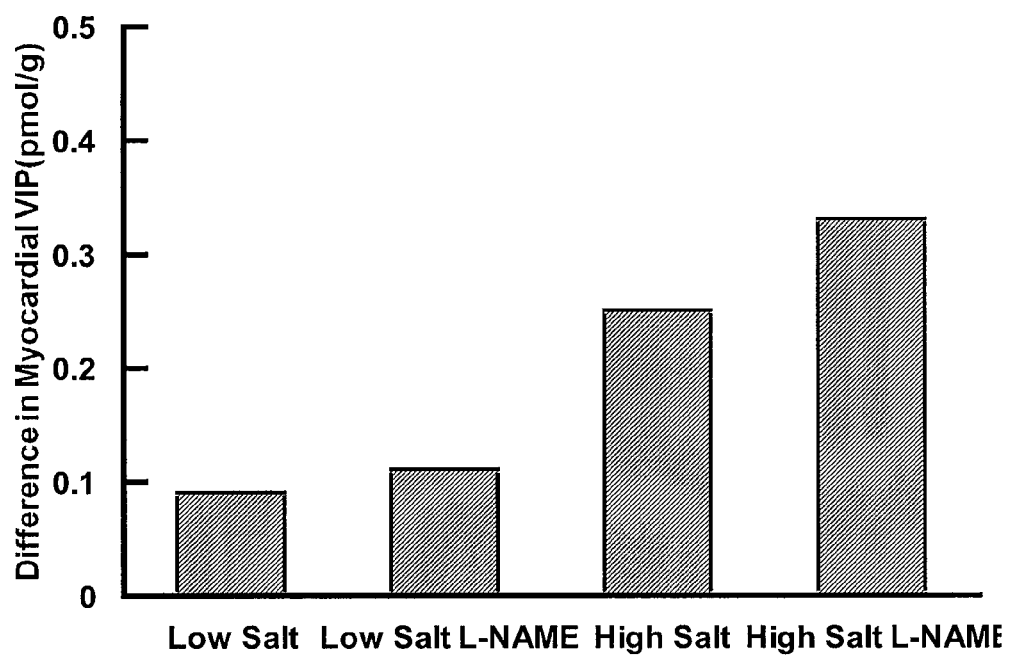

It has now been found, quite surprisingly in view of the negative indications, that VIP is useful and important as a therapeutic agent to reverse or delay onset of myocardial fibrosis, or prevent onset of fibrosis in subjects at risk of developing myocardial fibrosis. Thus, VIP is also useful in the treatment of congestive cardiac failure.

The use of the pharmaceutical compositions of the invention in the treatment of myocardial fibrosis or associated conditions represents a new class of therapeutic agent for these conditions. Existing treatments for myocardial fibrosis or associated conditions usually target one, or at the most two, of the known causative mechanisms in myocardial fibrosis. Without wishing to be bound by any particular mechanism of action, it is believed that the pharmaceutical preparations of the invention may target virtually all the currently known promoters of myocardial fibrosis. Further, VIP in the heart in normal concentrations may act to inhibit the production of profibrotic mediators. In addition to the role of VIP in sodium homeostasis and neurotransmission, VIP also appears to be a major modulator of the immune system, acting to down-regulate many of the cytokines involved in autoimmune inflammatory tissue damage. A number of cytokines, including but not limited to $IL_2$, $IL_{12}$, IFN-γ, TNF-α and TGF-β, which are known to cause fibrosis in both myocardium and other tissues, are down-regulated by VIP. VIP also down-regulates NF kappa B expression, translocation and binding by stabilising I kappa B. Further, VIP down-regulates the synthesis of another fibrotic mediator, angiotensin II (Ang II) via down-regulation of angiotensinogen synthesis.

On the basis of the present studies, and not wishing to be bound by theory, it is postulated that VIP acts as a major regulator to prevent the development of fibrosis and that the depletion of VIP may unleash the synthesis of a number of profibrotic mediators, thereby causing myocardial injury. The following scheme represents the hypothesised interactions between VIP and pro-fibrotic mediators.

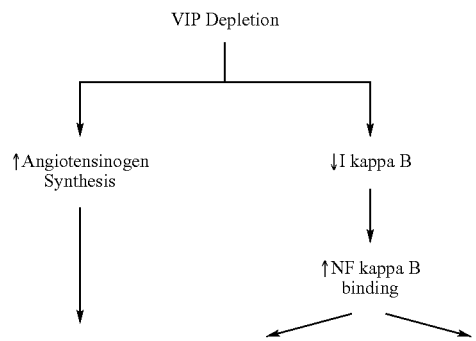

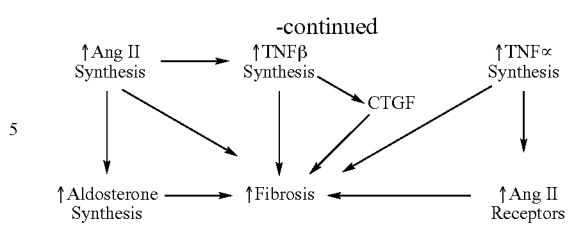

-continued

In the normal heart VIP is not taken up by the myocardium. However, in acute infusion studies the present inventors have found that uptake of VIP by the myocardium is more avid with increasing degrees of fibrosis suggesting the potential for VIP as a reparative agent.

The present studies have shown that certain VIP fragments have biological activities similar to those of the whole VIP molecule and may be better suited for pharmaceutical formulations due to their smaller size, greater stability and ease of manufacture. Particularly useful fragments are VIP(1-12) (SEQ ID No. 2) and VIP(6-28) (SEQ ID No. 3). It will be understood that the present invention also encompasses within its scope certain analogues of VIP which are based on conservative substitution of one or more amino acids of VIP with amino acids which do not alter the VIP biological activities. Such substitutions would be well known to those skilled in the art and would not require more than simple trial-and-error using well established techniques. Hence, the term "VIP" as used in the context of the present invention is intended to encompass such analogues.

The present invention also contemplates pharmaceutical compositions which include VIP and/or its active fragments. Such compositions may include any type of dosage form such as tablets, capsules, powders, liquid formulations, delayed or sustained release, patches, snuffs, nasal sprays and the like. The formulations may additionally include other ingredients such as dyes, preservatives, buffers and anti-oxidants, for example. The physical form and content of the pharmaceutical formulations contemplated are conventional preparations that can be formulated by those skilled in the pharmaceutical formulation field and are based on well established principles and compositions described in, for example, Remington: The Science and Practice of Pharmacy, $19^{th}$ Edition, 1995; British Pharmacopoeia 2000 and similar formulation texts and manuals. The compositions of the present invention may also include other active agents useful in the treatment of cardiovascular conditions.

The route and frequency of administration of the compositions of the present invention will depend on the treatment requirements and the nature of the molecule to be administered. Thus the formulations may be suitably prepared for administration by intravenous, intramuscular or subcuticular injection. VIP and VIP fragments may also be suitable for mucosal administration such as oral, sublingual, nasal and the like. These parameters are easily established by those skilled in the art.

The pharmaceutical compositions of the invention have been shown to be effective in preventing or slowing down progression of established myocardial fibrosis, as well as in reducing the degree (reversal) of established fibrosis and thus important in therapeutic applications. The compositions of the present invention are also useful form prophylactic or therapeutic treatment of congestive cardiac failure. These are important findings with respect to the range and severity of conditions which can be treated with the compositions of the present invention.

Further, the compositions of the present invention may be used prophylactically in subjects at risk of developing myocardial fibrosis or an associated condition. As an example of subjects in the risk category are those having hypertension, diabetes, myocarditis, ischaemic heart disease, drugs such as daunorubicin and others which are used in cancer chemotherapy, genetic predisposition, other conditions such as Conn's Syndrome and Phaeochromocytoma, high salt diet and the like. The term "prophylactic" as used in the context of the present invention is intended inter alia to encompass treatments used to prevent or slow down the development of fibrosis in the at risk group. High proportion of subjects which may be given prophylactic treatment may already have signs of early heart failure on echocardiography.

The term "associated condition" as used in the context of the present invention and in reference to myocardial fibrosis is intended to encompass, without limitation, left ventricular hypertrophy, diastolic dysfunction, myocarditis, cardiomyopathy, left ventricular dysfunction and congestive cardiac failure (for which myocardial fibrosis may be an underlying pathology). The associated condition may also include conditions which give rise to generation of profibrotic mediators or conditions which predispose a subject to myocardial fibrosis, such as for example hypertension and/or high salt intake, diseases such as diabetes and the like.

By elevating the VIP content of the cardiac muscle in a subject with, or at risk of developing, myocardial fibrosis or associated condition, through the use of the compositions of the present invention significant therapeutic benefits can be achieved including reduction of fibrosis, reduction in the level, production or activity of profibrotic mediators, reduction in progression of fibrosis, reduction in collagen formation or enhancing collagen degradation in the cardiac muscle.

The invention will now be described more particularly with reference to non-limiting examples.

EXPERIMENTAL

Example 1

Preliminary Studies

In preliminary studies a series of acute infusion experiments have been conducted in animal models. These showed that the higher the level of fibrosis, the greater the uptake of VIP by the heart from the plasma of the treated animals.

Further preliminary experiments have been conducted on a number of animal models, which encompass a range of fibrous tissue replacement, varying from mild to moderate to severe. The experiments on the animal models encompassed a variety of aetiologies (alone and in combination) and a range of levels of induced fibrosis. For these experiments two types of rats were used, spontaneously hypertensive rats (SHR) and normotensive control Wistar-Kyoto rats (WKY). The WKY rats were given: 1) low salt diet, 2) high salt diet, or 3) L-NAME (ω-monomethyl-nitro-L-arginine; 10 mg/kg/day) plus high salt diet. The SHR rats were given low or high salt diets. The effect of VIP infusion in diabetic heart disease was also studied in the WKY rate with streptozotocin induced diabetes.

In each treatment group, rats were randomised to VIP (SEQ ID No. 1) or vehicle infusion (n=24 in each group) for four weeks. VIP was administered via Alzet mini pump at a rate of 7.2 nmol/kg/day.

After four weeks, the rats were anaesthetised and the hearts were harvested. Myocardial VIP concentrations and myocardial fibrosis were quantitated. A significant improvement was found in the hearts of the treated rats in that the myocardial fibrosis index was significantly lower in the treated rats compared to the control groups.

Example 2

Effect of VIP Infusion on Myocardial VIP Concentrations

Fourteen week old WKY rats were randomised to low salt diet (0.008%), intermediate salt diet (2.2%), high salt diet (4.4%) or high salt diet plus L-NAME (10 mg/kg/day) in the drinking water for 4 weeks (n=16 rats per group). On the day of the experiment the rats were anaesthetised and venous and arterial cannulae inserted. After a one hour rest equilibration period the rats were randomised to vehicle control (Haemaccell, Aventis) or VIP (10 pmol/kg/min) infusion (SEQ ID No. 1) for one hour at an infusion rate of 0.017 ml/min. The hearts were then harvested, myocardial VIP concentrations were measured and myocardial fibrosis quantitated.

The difference between the mean myocardial VIP concentrations after VIP or control infusion is a measure of VIP uptake by the heart. This difference was found to increase as the degree of fibrosis increased (see FIG. 1).

Example 3

Effect of VIP Infusion on Fibrosis in Animal Models of Fibrosis

Three animal models of myocardial fibrosis were used (animals obtained from Australian Animal Resources, Perth, Western Australia, Australia)
i) WKY rat fed a high salt diet
ii) WKY rat fed a high salt diet and given L-NAME (ω-monomethyl-nitro-L-arginine, Sigma Chemical Co.) 10 mg/kg/day in the drinking water
iii) WKY rats with diabetes induced by streptozotocin injection 60 mg/kg In each model the rats were randomised to VIP (H-His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn-$NH_2$, (SEQ ID No. 1) obtained from Auspep, Australia) or vehicle control (Haemaccel, Aventis) infusion for 4 weeks via Alzet minipump (n=6-8 each experimental group). The dose of VIP was 5 pmol/kg/min.

In models i) and ii) 14 week old WKY rats were commenced on high salt diet or high salt diet plus L-NAME. They underwent operative insertion of an Alzet minipump for infusion of VIP or vehicle. After 4 weeks the rats were anaesthetised and the hearts harvested. Myocardial VIP and myocardial fibrosis were quantitated.

In model iii) rats were injected with streptozotocin 60 mg/kg at 14 weeks of age. After 8 weeks the diabetic rats were randomised to VIP infusion (5 pmol/kg/min) (SEQ ID No. 1) or no treatment. VIP was administered as above. After a further 4 weeks the rats were anaesthetised and the hearts harvested as above.

Myocardial VIP concentrations and myocardial fibrosis were quantitated.

VIP was measured by radioimmunoassay in known manner (see Davis R. E., Shelley S., Macdonald G. J. & Duggan K. A. (1992) The effects of a high sodium diet on the metabolism and secretion of vasoactive intestinal peptide in the rabbit. J. Physiol. 451:17-23. Duggan K. A., Ye V. Z. C., Jones D. M. Davis R. E. & Macdonald G. J. (1995) Effects of Endopeptidase 24.11 blockade on plasma and tissue concentrations of vasoactive intestinal peptide Clin. Sci. 89:267-271). The degree of myocardial fibrosis was quantitated by two methods in known manner (refer Ye V Z C, Hodge G, Yong J L C & Duggan K A (2002) Early myocardial fibrosis is associated with depletion of vasoactive intestinal peptide in the heart Exp. Physiol 87:539-546 Ye V Z C, Hodge G, Yong J L C & Duggan K A (2003) Myocardial VIP and myocardial fibrosis induced by nitric oxide synthase inhibition in the rat Acta Physiol. Scand. 179:353-360. Ye V Z C, Hodge G, Yong J L C & Duggan K A (2004) Vasopeptidase inhibition reverses myocardial VIP depletion and decreases myocardial fibrosis in salt sensitive hypertension Europ. J. Pharmacol. 485:235-242).

Figure 2:
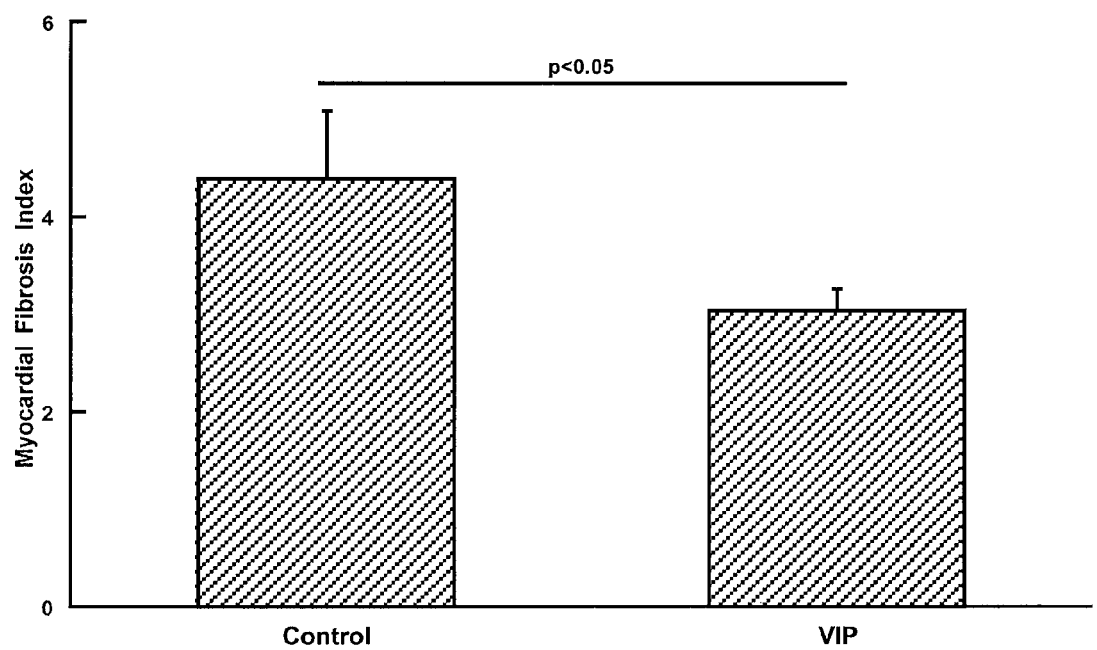
FIG. 2: Myocardial fibrosis index in WKY rats after 4 weeks on a high salt diet and either VIP (SEQ ID No. 1) or vehicle Control infusion.
Figure 3:
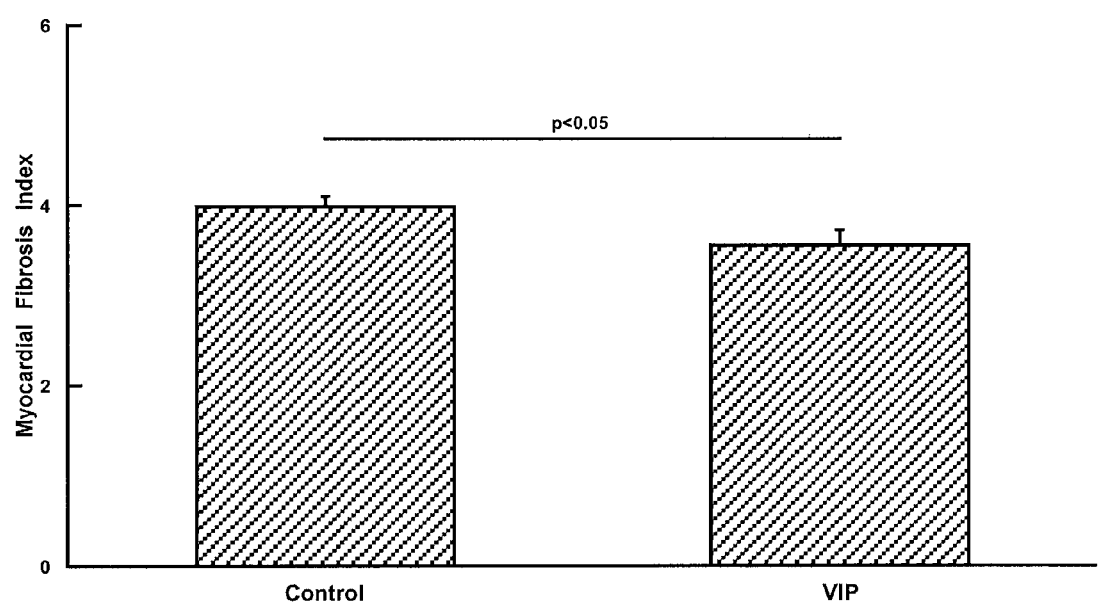
FIG. 3: Myocardial fibrosis index in WKY rats on a high salt diet plus L-NAME (10 mg/kg/day) for 4 weeks receiving either vehicle Control or VIP (SEQ ID No. 1) infusion.

A significant improvement was found in the hearts of the treated rats in that the myocardial fibrosis index was significantly lower in the treated rats compared to the control groups (FIGS. 2 and 3).

Example 4

Figure 4:
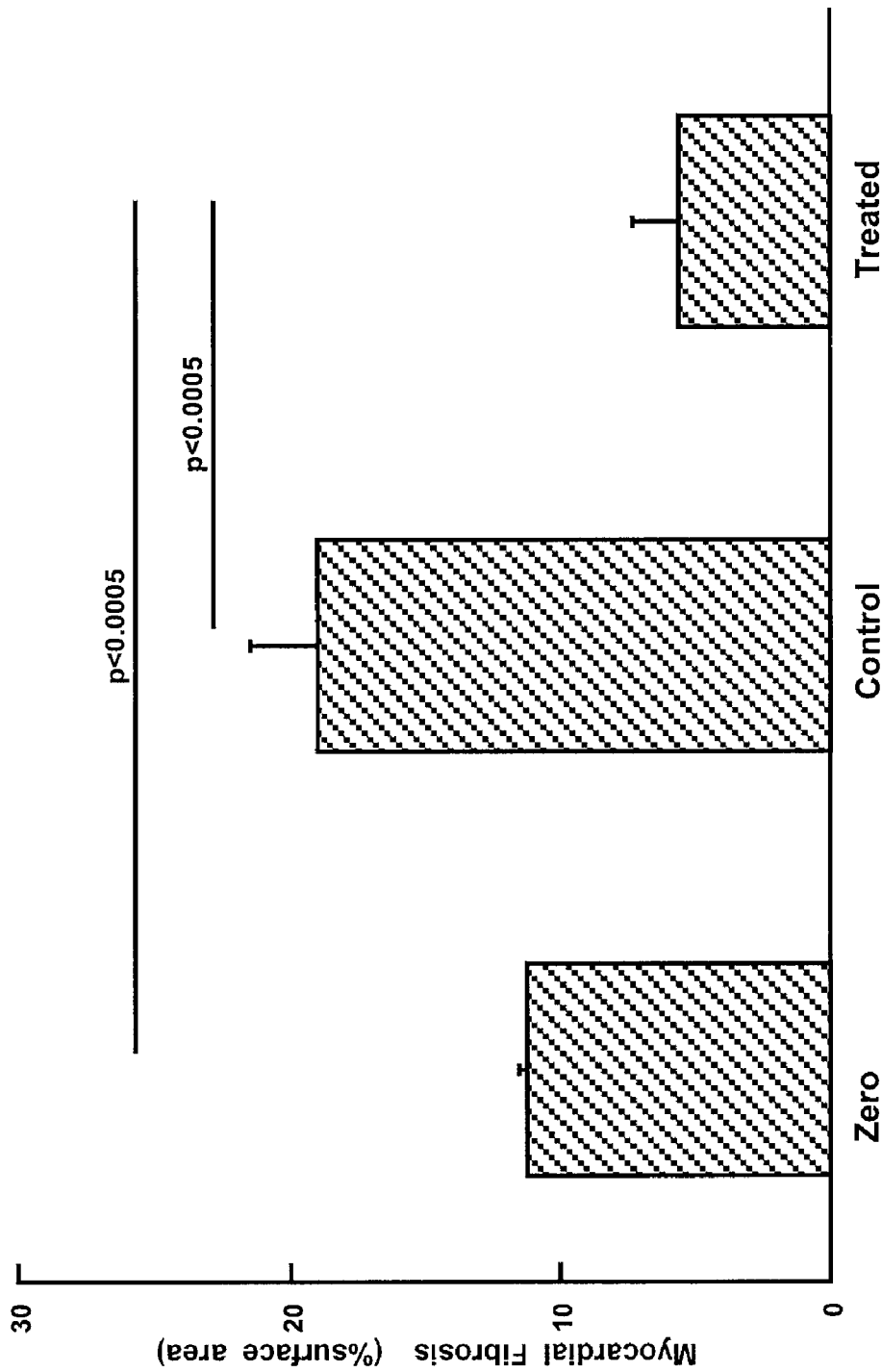
FIG. 4: Myocardial fibrosis in rats aged 14 weeks (zero time) then on high salt diet for 4 weeks and receiving either vehicle infusion or VIP infusion (SEQ ID No. 1) (5 pmol/kg/min) for 4 weeks.
Figure 5:
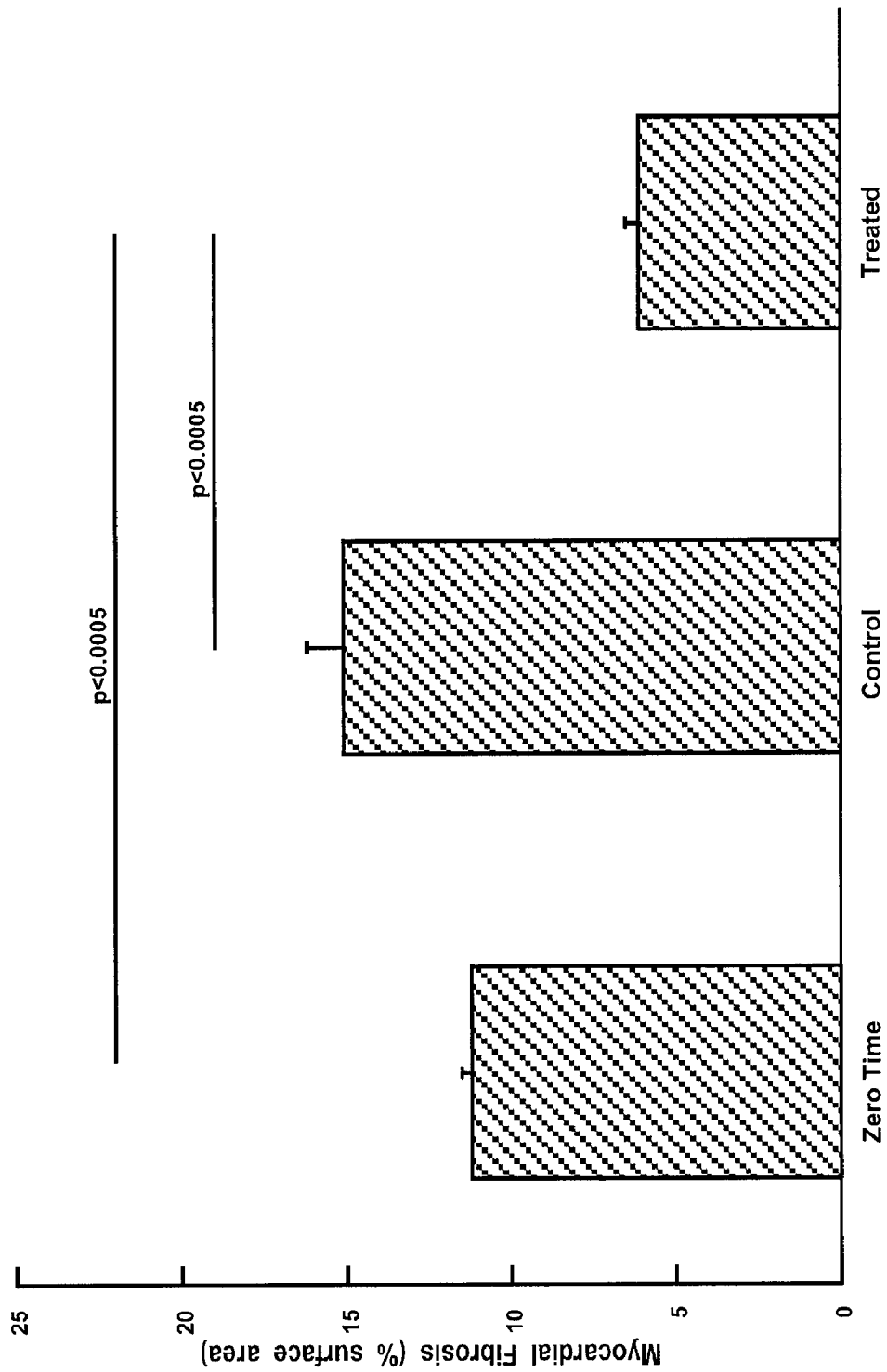
FIG. 5: Myocardial fibrosis in rats aged 14 weeks (zero time) then on high salt diet plus L-NAME (10 mg/kg) in the drinking water for 4 weeks and receiving either vehicle infusion or VIP infusion (SEQ ID No. 1) (5 pmol/kg/min) for 4 weeks.

Effect of VIP Treatment on Myocardial VIP Content and Regression of Fibrosis in Animal Models of Fibrosis To determine whether VIP infusion caused regression of existing fibrosis as well as prevented progression of fibrosis two groups of studies were performed i) the degree of myocardial fibrosis in untreated 14 week old WKY rats was compared with the degree of fibrosis in 18 week old WKY rats after 4 weeks treatment with a high salt diet or a high salt diet plus L-NAME (10 mg/kg/day) and either VIP (SEQ ID No. 1) (5 pmol/kg/min) or control infusion (see FIGS. 4 and 5)

ii) non-diabetic control WKY were sacrificed at 26 weeks of age and the degree of myocardial fibrosis was compared with that in WKY rats which had had diabetes induced by streptozotocin injection (60 mg/kg) at 14 weeks. After 8 weeks of diabetes the rats were randomised to VIP infusion (SEQ ID No. 1) (5 pmol/kg/min) via Alzet minipump or no treatment for a further 4 weeks. (see FIG. 6)

Figure 6:
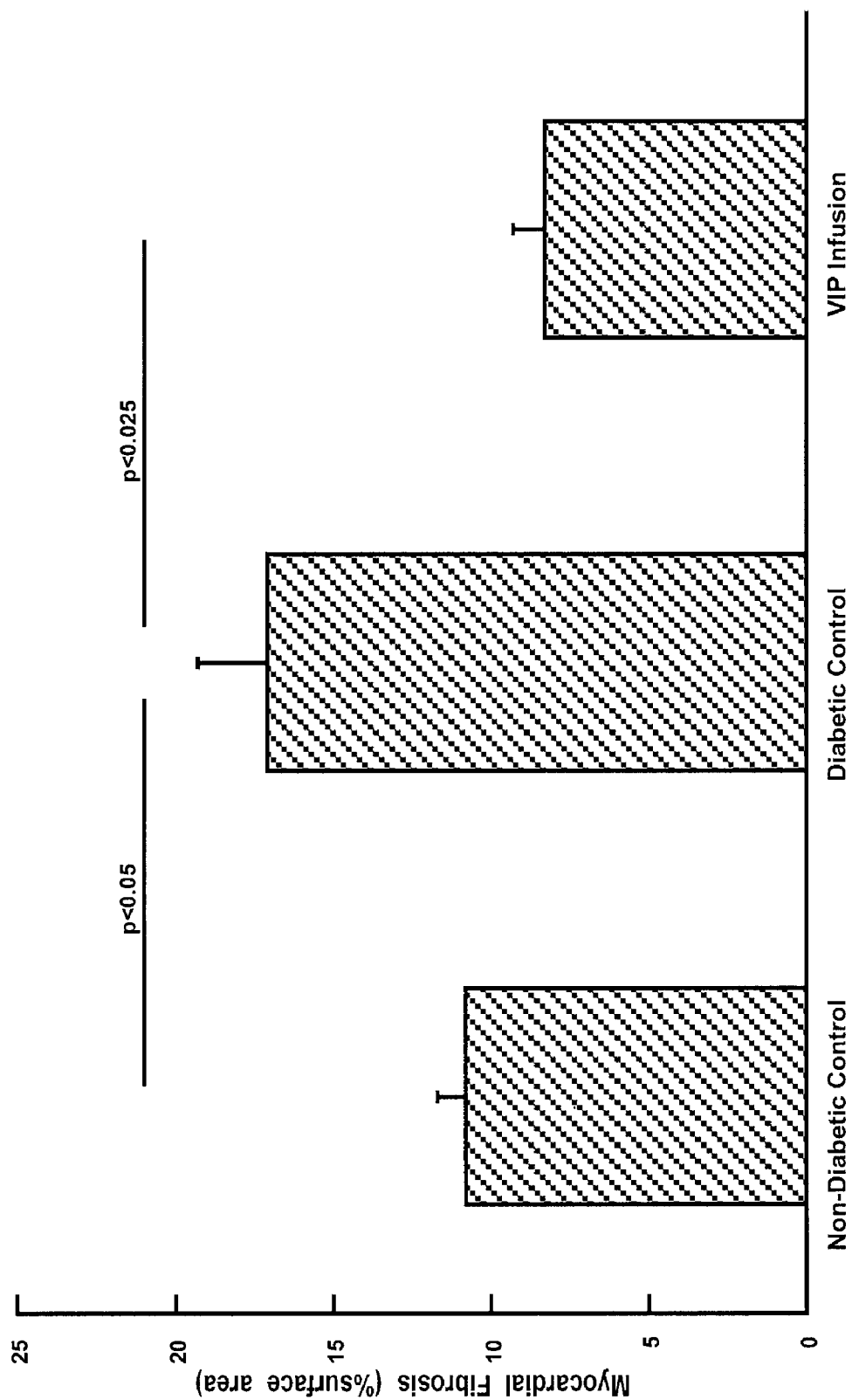
FIG. 6: Myocardial fibrosis in WKY rats treated with streptozotocin (60 mg/kg) at 14 weeks. After 8 weeks diabetes VIP infusion (SEQ ID No. 1) was commenced in some rats and continued for 4 weeks. All rats were sacrificed at 26 weeks of age.

Results are shown in FIGS. 4 to 6. The data clearly show regression of myocardial fibrosis in the three models following VIP infusion. The diabetic rat model demonstrates the same action of VIP in a model which is not related to salt intake or high blood pressure. The regression of fibrosis may be due to either reduction in collagen formation or enhancement of its degradation. Although not wishing to be bound by any particular mechanism of action, the regression of myocardial fibrosis is likely to be due to the action of collagenases, which play a part in collagen resorption.

Figure 7:
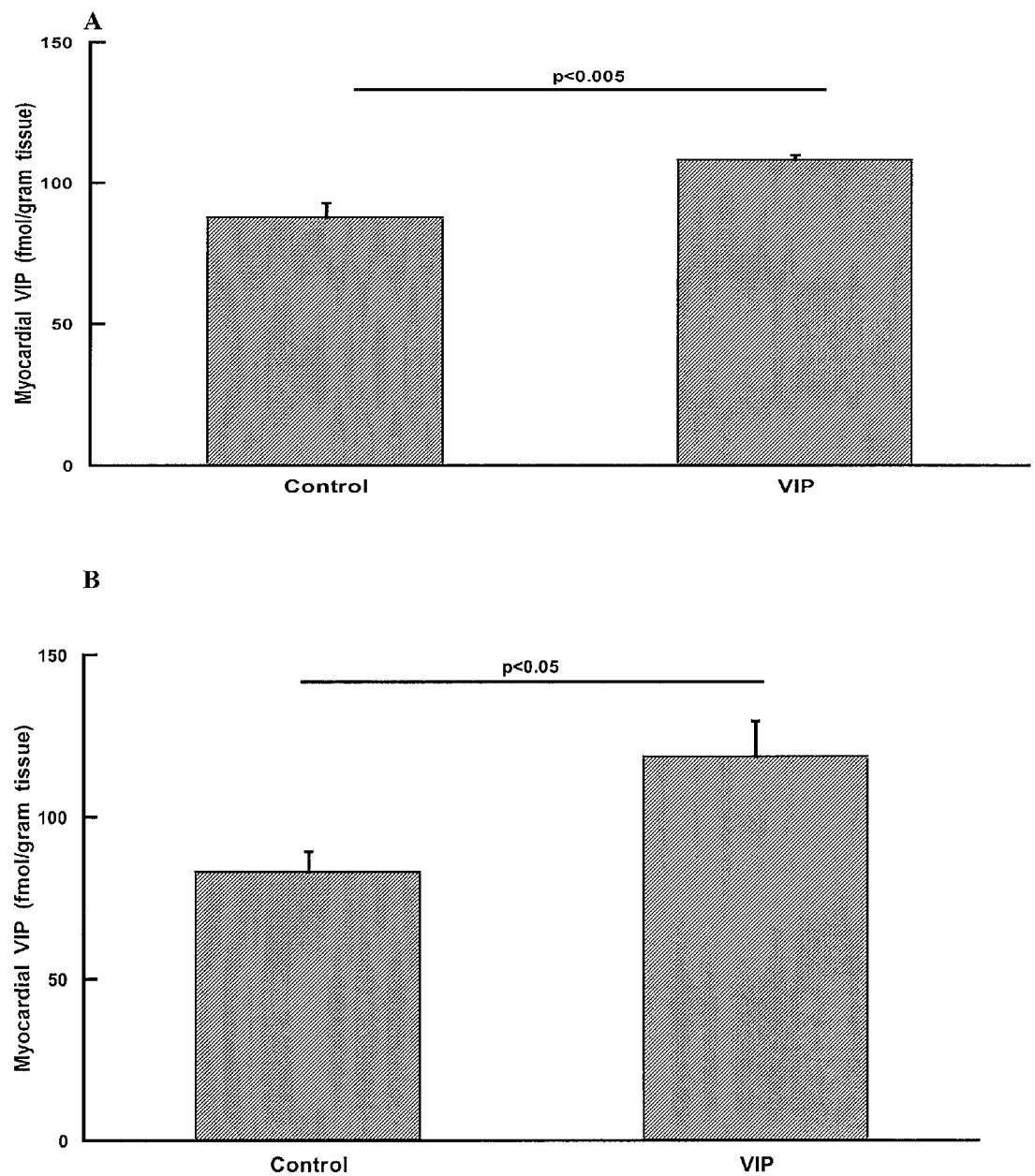
FIG. 7: A—Myocardial VIP concentrations in WKY rats on a high salt diet after a four week intravenous infusion of VIP (SEQ ID No. 1) or vehicle control. B—Myocardial VIP concentrations in WKY rats on a high salt diet and L-NAME (10 mg/kg) in the drinking water after a four week intravenous infusion of VIP (SEQ ID No. 1) or vehicle control.

Measurement of myocardial content of VIP in the above animal models shows a clear association between the degree of fibrosis and uptake of exogenous VIP (see FIGS. 7A and 7B)

Example 5

Effect of VIP Fragments on Myocardial Fibrosis

To determine whether smaller VIP related peptides had any of the biological activities of the complete VIP molecule, particularly in reducing myocardial fibrosis, the degree of myocardial fibrosis after treatment with VIP(1-12) (SEQ ID No. 2) at 5 pmol/kg/min and VIP (6-28) (SEQ ID No. 3) at 5 pmol/kg/min for 4 weeks via Alzet minipump was compared with the complete VIP (5 pmol/kg/min) (SEQ ID No. 1) and vehicle control. The VIP fragments were purchased from Auspep (Melbourne, Australia).

Figure 8:
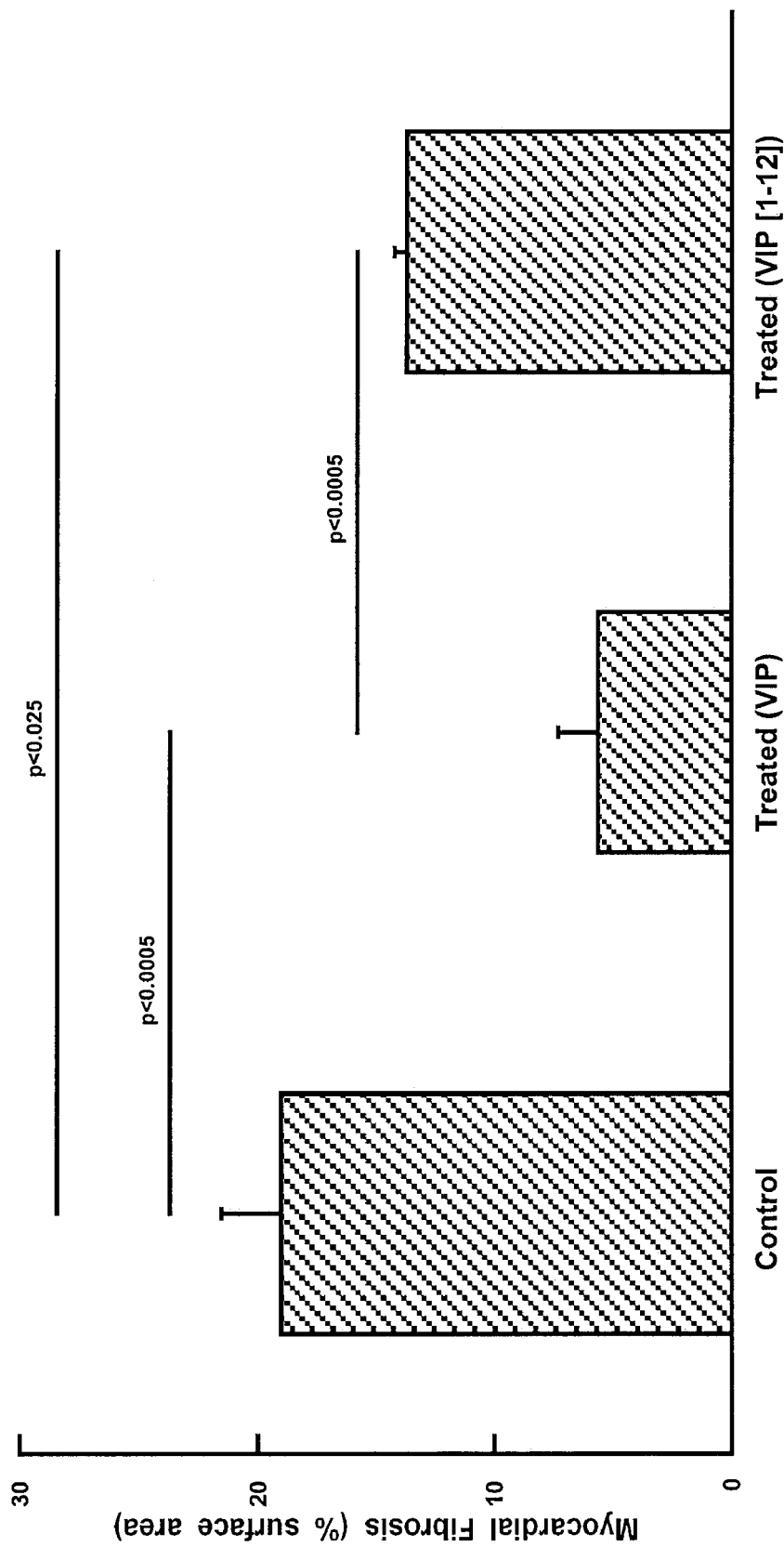
FIG. 8: Comparison of the effects of treatment with peptide VIP(1-12) (SEQ ID No. 2) and with complete VIP molecule (SEQ ID No. 1) on myocardial fibrosis. Both peptides were given at a dose of 5 pmol/kg/min for 4 weeks intravenously.
Figure 9:
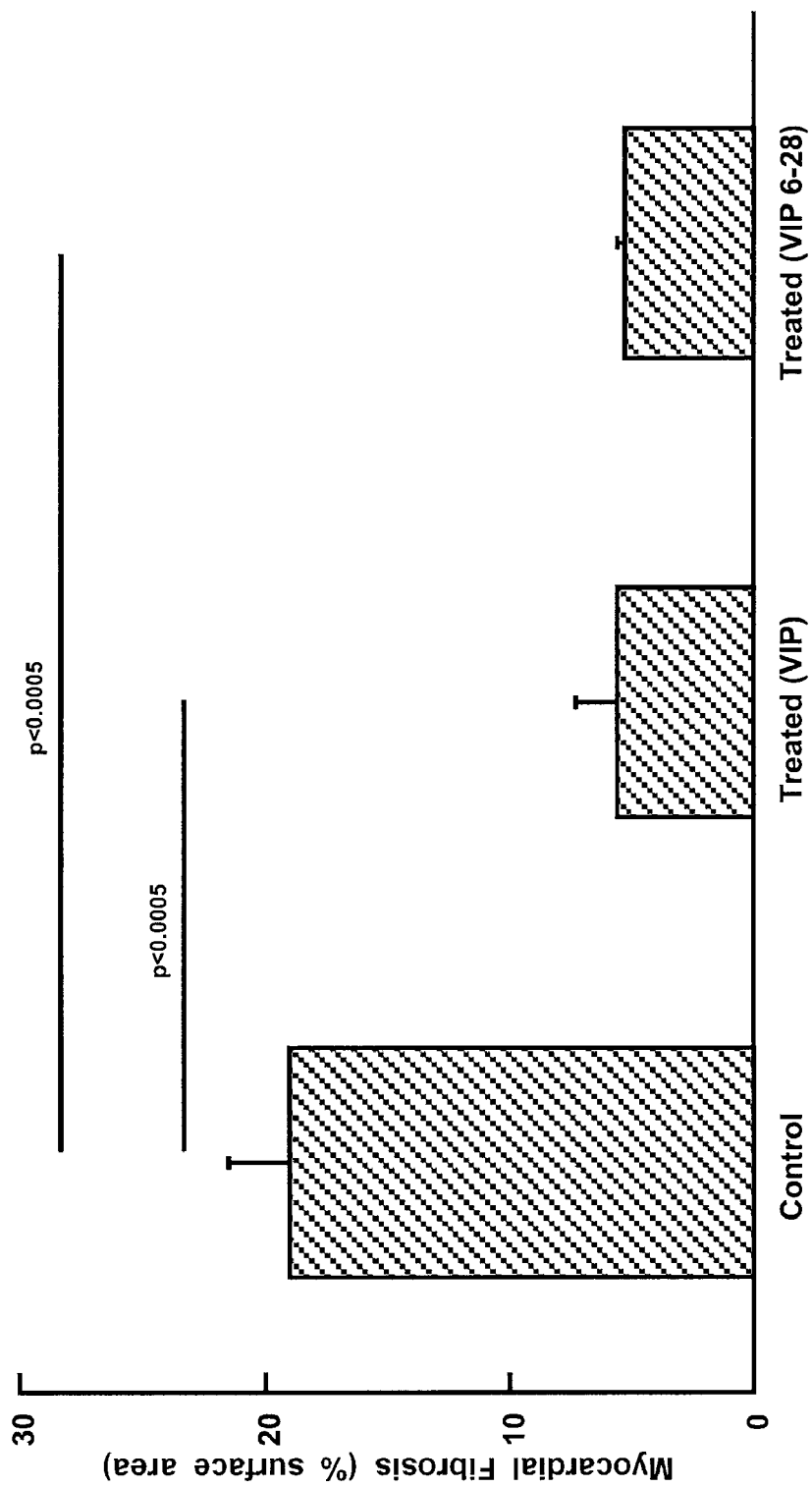
FIG. 9: Comparison of the effects of treatment with peptide VIP(6-28) (SEQ ID No. 3) and with complete VIP molecule (SEQ ID No. 1) on myocardial fibrosis. Both peptides were given at a dose of 5 pmol/kg/min for 4 weeks intravenously.
Figure 10:
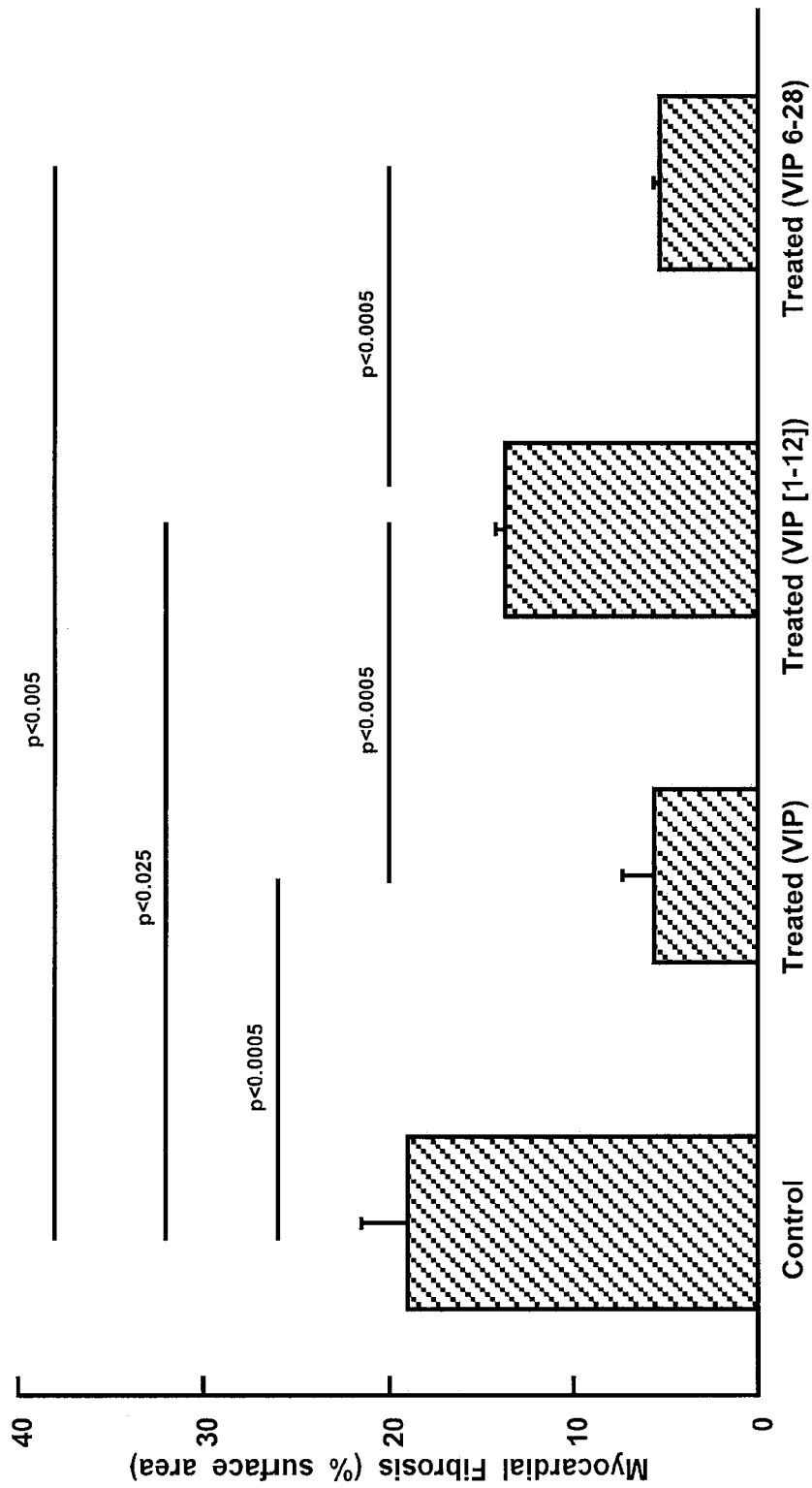
FIG. 10: Comparison of the effects of treatment with peptides VIP(1-12) (SEQ ID No. 2), VIP(6-28) (SEQ ID No. 3) and with complete VIP molecule (SEQ ID No. 1) on myocardial fibrosis. All peptides were given at a dose of 5 pmol/kg/min for 4 weeks intravenously.

Briefly, 14 week old WKY rats were commenced on high salt diet as described earlier. They underwent operative insertion of an Alzet minipump for infusion of VIP peptide or vehicle. After 4 weeks the rats were anaesthetised, the hearts harvested and myocardial fibrosis quantitated on Masson Trichrome sections using Image Pro Plus Version 5 (Cybernetics). Both VIP(1-12) (SEQ ID No. 2) and VIP(6-28) (SEQ ID No. 3) decreased the degree of myocardial fibrosis compared with vehicle control. VIP(1-12) (SEQ ID No. 2) was approximately ⅓ as effective as VIP (SEQ ID No. 1) whereas VIP(6-28) (SEQ ID No. 3) was as effective as VIP (SEQ ID No. 1). FIGS. 8 to 10 show the results of these studies.

The importance of the present invention to health care will be immediately apparent to one skilled in the art upon reading this disclosure. Although the capacity to treat cardiac failure has improved significantly with the advent of angiotensin converting enzyme (ACE) inhibitors and angiotensin receptor blockers, as well as the realisation that aldosterone antagonists and beta blockers improve outcome in later stage disease, the addition of the pharmaceutical preparation of the invention, which acts to prevent the progression of the underlying lesion (fibrosis), or even reverse fibrosis, has the capacity to prevent the escalation of mild to severe disease and hence to substantially reduce the health care burden.

It is to be appreciated that other embodiments are available for the composition, method and use of the invention and that these are within the scope of the invention.

The invention claimed is:

1. A method of therapeutic treatment of myocardial fibrosis in a subject, the method comprising administering to the subject with myocardial fibrosis, a composition comprising one or more of vasoactive intestinal peptide (VIP) (SEQ ID No. 1) or an active fragment thereof, optionally in combination with a pharmaceutically acceptable carrier, wherein the active fragment is VIP (1-12) (SEQ ID No. 2) and/or VIP (6-28) (SEQ ID No. 3).

2. A method of reducing or inhibiting the levels or the production of pro-fibrotic mediators in a subject with myocardial fibrosis, the method comprising administering to the subject with myocardial fibrosis a composition comprising one or more of vasoactive intestinal peptide (VIP) (SEQ ID No. 1) or an active fragment thereof, optionally in combination with a pharmaceutically acceptable carrier, wherein the active fragment is VIP (1-12) (SEQ ID No. 2) and/or VIP (6-28) (SEQ ID No. 3).

3. A method of elevating the VIP content of the cardiac muscle in a subject with myocardial fibrosis, the method comprising administering to the subject with myocardial fibrosis a composition comprising one or more of vasoactive intestinal peptide (VIP) (SEQ ID No. 1) or an active fragment thereof, optionally in combination with a pharmaceutically acceptable carrier, wherein the active fragment is VIP (1-12) (SEQ ID No. 2) and/or VIP (6-28) (SEQ ID No. 3).

4. A method of reducing collagen formation or enhancing collagen degradation in the cardiac muscle of a subject with myocardial fibrosis, the method comprising administering to the subject with myocardial fibrosis a composition comprising one or more of vasoactive intestinal peptide (VIP) (SEQ ID No. 1) or an active fragment thereof, optionally in combination with a pharmaceutically acceptable carrier, wherein the active fragment is VIP (1-12) (SEQ ID No. 2) and/or VIP (6-28) (SEQ ID No. 3).

5. A method according to claim 1, 2, 3 or 4, wherein the composition is administered by a route selected from the group consisting of intravenous, intramuscular, subcuticular and oral.

6. The method of claim 1, 2, 3 or 4, wherein the subject is at risk of developing congestive cardiac failure.

7. A method according to claim 1, 2, 3 or 4, wherein the subject with myocardial fibrosis has a further condition selected from the group consisting of hypertension, ischaemic heart disease, left ventricular hypertrophy, diastolic dysfunction, myocarditis, cardiomyopathy, left ventricular dysfunction and congestive cardiac failure.

8. A method according to claim 1, 2, 3 or 4, wherein the composition is administered in conjunction with at least one other therapeutic agent for the therapeutic treatment of myocardial fibrosis.

9. A method according to claim 6 wherein the composition is administered in conjunction with at least one other therapeutic agent for the therapeutic treatment of myocardial fibrosis.

* * * * *